(12) United States Patent (10) Patent No.: US 7,425,694 B2
Nishizawa et al. (45) Date of Patent: Sep. 16, 2008

(54) TIME-RESOLVED MEASUREMENT APPARATUS

(75) Inventors: Mitsunori Nishizawa, Hamamatsu (JP); Nobuyuki Hirai, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 10/561,938

(22) PCT Filed: Jun. 24, 2004

(86) PCT No.: PCT/JP2004/009268

§ 371 (c)(1),
(2), (4) Date: Mar. 20, 2007

(87) PCT Pub. No.: WO2004/113888

PCT Pub. Date: Dec. 29, 2004

(65) Prior Publication Data

US 2007/0267565 A1 Nov. 22, 2007

(30) Foreign Application Priority Data

Jun. 24, 2003 (JP) ............................. 2003-179775

(51) Int. Cl.
*H01J 40/14* (2006.01)
(52) U.S. Cl. .............................. 250/207; 250/214 VT; 313/542; 313/103 CM; 313/104; 313/105 R; 313/105 CM

(58) Field of Classification Search ........... 240/214 VT, 240/207, 214.1; 313/542, 103 CM, 104, 313/105 R, 105 CM; 356/622
See application file for complete search history.

(56) References Cited

U.S. PATENT DOCUMENTS 5,180,908 A * 1/1993 Suyama ................. 250/214 VT
5,221,836 A * 6/1993 Kinoshita ............. 250/214 VT

FOREIGN PATENT DOCUMENTS

| JP | 60-220542 | 11/1985 |
| JP | 61-266942 | 11/1986 |
| JP | 07-211280 | 8/1995 |
| JP | 10-150086 | 6/1998 |

* cited by examiner

*Primary Examiner*—Stephen Yam
(74) *Attorney, Agent, or Firm*—Drinks Biddle & Reath LLP

(57) ABSTRACT

A time-resolved measurement apparatus (100) acquires a detection timing pulse from an output terminal (34) attached to a micro channel plate (30) in a photomultiplier tube (14). A position-time measuring circuit (16) generates a signal indicating the time difference between a reference time pulse synchronized with excitation of a sample (10) and the detection timing pulse, and feeds the signal to a data processor (18). The data processor stores this time difference as a detection time of light emission. The data processor corrects the detection time according to the distance between the position at which the detection timing pulse is generated on the micro channel plate and the output terminal. This enhances the precision of time-resolved measurement.

7 Claims, 13 Drawing Sheets

TIME-RESOLVED MEASUREMENT APPARATUS

TECHNICAL FIELD

The present invention relates to a time-resolved measurement apparatus using a position-sensitive electron multiplier tube (PS-EMT).

BACKGROUND ART

There are known two-dimensional time-resolved measurement apparatus for performing time-resolved measurement of light emission to acquire the two-dimensional position and time thereof. Such apparatus are disclosed in Japanese Patent Application Laid-Open No. 61-266942, Japanese Patent Application Laid-Open No. 10-150086, and Article "Two-dimensional time-resolved imaging with 100-ps resolution using a resistive anode photomultiplier tube" by S. Charbonneau et al. (Rev. Sci. Instrum. 63 (11), USA, American Institute of Physics, November 1992, pp 5315-5319).

DISCLOSURE OF THE INVENTION

An object of the present invention is to enhance the precision of time-resolved measurement.

A time-resolved measurement apparatus according to the present invention acquires position information and timing information of a quantum beam generated due to excitation of a sample. This time-resolved measurement apparatus comprises: a signal generator for generating a reference time pulse in synchronization with the excitation of the sample; a detector for detecting the quantum beam from the sample and for generating a position signal corresponding to a detection position, and a detection timing pulse synchronized with a detection timing; a position calculator for calculating the detection position using the position signal; a time difference measuring device for measuring the time difference between the reference time pulse and the detection timing pulse; and a data processor for storing the detection position calculated by the position calculator and the time difference measured by the time difference measuring device, in association with each other. The detector has a position-sensitive electron multiplier tube. This electron multiplier tube has a micro channel plate for generating an electron at a position corresponding to an incidence position of the quantum beam on the electron multiplier tube and for multiplying the electron while maintaining the position; and an output terminal electrically connected to the micro channel plate. The detection timing pulse is generated in response to a potential change that occurs when the electrons multiplied by the micro channel plate are emitted from the micro channel plate, and are fed from the micro channel plate to the time difference measuring device through the output terminal. The data processor corrects the time difference according to the distance between a position at which the detection timing pulse is generated on the micro channel plate and the output terminal, and stores the corrected time difference in association with the detection position.

Since the micro channel plate maintains the position information of the quantum beam, the detection timing pulse is generated on the micro channel plate at a position corresponding to a position at which the quantum beam is generated on the sample. Therefore, quantum beams emitted from different positions on the sample generate detection timing pulses at different positions on the micro channel plate. A time necessary for a generated detection timing pulse to reach the output terminal is dependent on the distance between the position at which the detection timing pulse is generated and the output terminal. For this reason, quantum beams generated at the same timing from different positions on a sample can generate detection timing pulses reaching the output terminal at different timings, thus producing different time differences. In the present invention, the data processor corrects the time difference according to the distance between the generation position of the detection timing pulse and the output terminal to cancel the error of the time difference according to the variation in the generation positions of the quantum beams. Consequently, it is possible to enhance the precision of time-resolved measurement.

The quantum beam embraces charged particles which are, for example, electrons, ions, $\alpha$-rays, $\beta$-rays and the like, photons which are, for example, ultraviolet rays, X-rays, $\gamma$-rays and the like, and further embraces neutrons and others. The generation of the quantum beam due to the excitation of the sample is a phenomenon in which an atom, a molecule, or the like transfers from a low energy state to a higher energy state by external stimulation such as heat, light, radiation or the like, and returns from the excited state to the low energy state while emitting the difference between the energies in the two states as a quantum beam such as light (cf. the aforementioned Patent Document 1 and Non-patent Document 1). It is also known that when a semiconductor device is activated spontaneously or in response to an external trigger (signal pulse, operation start pulse, or the like), transient emission occurs in conjunction with a switching operation of a transistor in the device (cf. the aforementioned Patent Document 2). The generation of the quantum beam due to the excitation of the sample in the present invention also embraces the transient emission observed upon the operation of semiconductor devices, in addition to the phenomenon in which an atom or molecule emits the difference between energies in two states as a quantum beam such as light.

The data processor may be arranged to correct the time difference by removing a time necessary for the detection timing pulse to reach the output terminal from its generation position, from the time difference measured by the time difference measuring device. In this case, a component dependent upon the distance between the generation position of the detection timing pulse and the output terminal is removed from the time difference. This results in canceling the error of the time difference according to the variation in the generation positions of the quantum beams and thus enhancing the precision of time-resolved measurement.

The data processor may be arranged to set a plurality of sampling points on the micro channel plate, acquire and interpolate correction data for the detection timing pulse generated at each sampling point, and correct the time difference using the interpolated correction data. The interpolation method allows a number of correction data to be calculated from a small number of samples. Consequently, it is possible to reduce the time necessary for acquisition of the correction data.

The data processor may accumulate the detection position and the time difference over plural times of the excitation of the sample. This is advantageous in measurement of a sample having a low probability of generation of the quantum beam.

The data processor may use the accumulated time differences to create a histogram of the time differences in association with a specific detection position. This histogram can be used for determining the timing of generation of the quantum beam at a position. The quantum beam generation timing thus determined can be utilized for an analysis of operation of semiconductor devices that can emit quantum beams with a low probability upon their operation.

The sample may have a circuit including a plurality of semiconductor devices that can emit quantum beams upon their operation. The excitation of the sample may be to activate the circuit so as to operate the semiconductor devices in turn. The data processor may be arranged to specify the detection positions corresponding to the positions of the semiconductor devices, and to calculate the time differences corresponding to peaks in the histograms for the specified detection positions. The peak in the histogram indicates a time difference with which the generation of the quantum beams at a detection position has been detected at the highest frequency. Therefore, this time difference can be treated as a timing at which the quantum beam has been generated from the semiconductor device corresponding to the detection position. By calculating the timings of quantum beam generation for the semiconductor devices, it is feasible to analyze the operation of the circuit including those semiconductor devices.

The electron multiplier tube may be a position-sensitive photomultiplier tube having a photocathode for converting the quantum beam into a photoelectron by photoelectric effect. In this case, the micro channel plate is located opposite the photocathode and receives the photoelectron from the photocathode to generate and multiply secondary electrons.

The foregoing and other objects and novel features of the present invention will become more fully apparent in view of the following description with reference to the accompanying drawings. It is, however, noted that the drawings are presented for illustrative purposes only and do not limit the technical scope of the present invention.

BEST MODE FOR CARRYING OUT THE INVENTION

Figure 1:
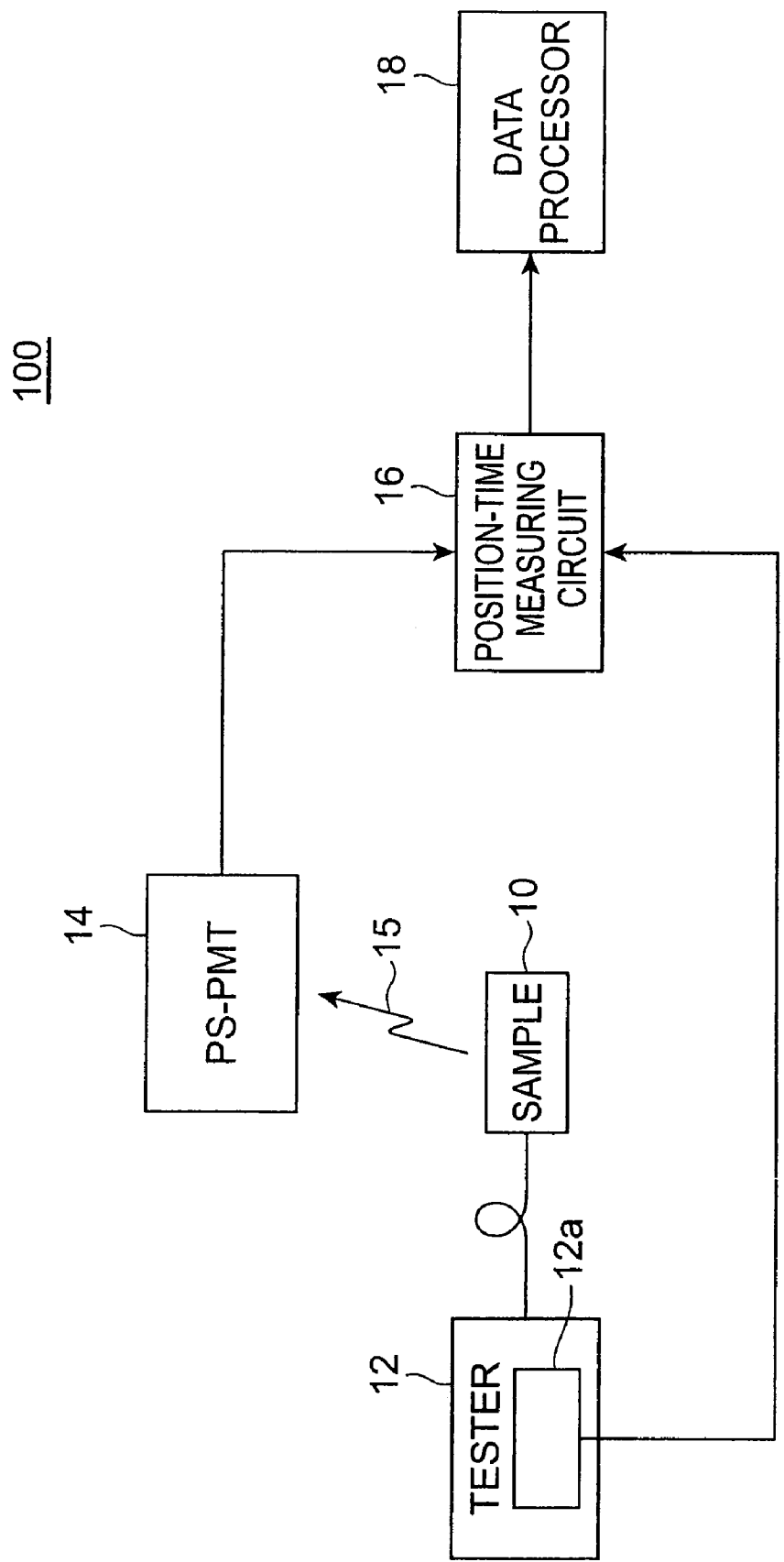
FIG. 1 is a block diagram showing the configuration of a time-resolved measurement apparatus according to an embodiment.

Preferred embodiments of the present invention will be described below in detail with reference to the accompanying drawings. For easier understanding, identical or equivalent elements common to the drawings will be denoted by similar reference numerals, without redundant description.

FIG. 1 is a block diagram showing the configuration of a time-resolved measurement apparatus 100 according to the present embodiment. The apparatus 100 detects light 15 emitted from a sample 10 and measures the two-dimensional position and timing of the emission. The apparatus 100 has a semiconductor tester 12, position-sensitive photomultiplier tube (PS-PMT) 14, position-time measuring circuit 16, and data processor 18.

Figure 2:
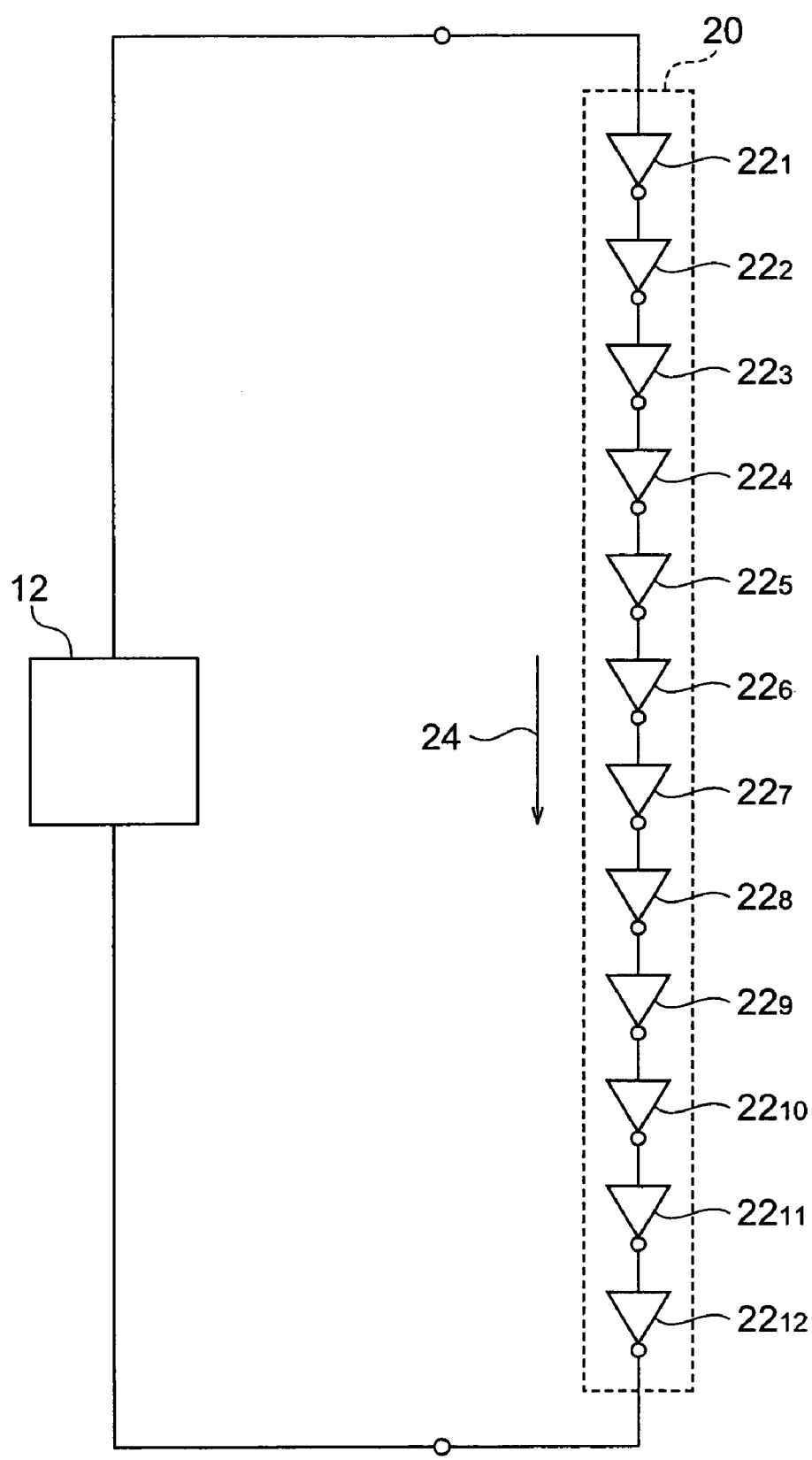
FIG. 2 is a schematic view showing an integrated circuit contained in a sample.

In the present embodiment, a chip having a semiconductor integrated circuit (IC) thereon is prepared as an example of the sample 10. FIG. 2 is a schematic view showing the IC on the sample 10. This IC is an inverter chain 20 having twelve inverters $22_1$-$22_{12}$ connected in series. In the inverter chain 20, a signal sequentially propagates from the first inverter $22_1$ to the last inverter $22_{12}$ along a direction shown as arrow 24. The signal propagation time between two adjacent inverters is theoretically designed as 70 ps. A MOS transistor forming an inverter sometimes emits light upon its switching. Therefore, by measuring the position and timing of the emission using the apparatus 100, it is feasible to determine when and which transistor is switched. This enables an analysis of operation of the inverter chain 20.

The semiconductor tester 12 is an excitation device for exciting the sample 10 to cause emission of light. The tester 12 is electrically connected to the inverter chain 20 on the sample 10 and applies a drive voltage thereto. The tester 12 includes a signal generator 12a for generating a time reference pulse in synchronization with the application of the drive voltage. The time reference pulse is fed to the position-time measuring circuit 16.

The position-sensitive photomultiplier tube 14 converts the light from the sample 10 into electrons and multiplies the electrons while maintaining the two-dimensional position thereof. The photomultiplier tube 14 has a photocathode, a micro channel plate (MCP), and a resistive anode. The micro channel plate is located between the photocathode and the resistive anode. The front face of the micro channel plate is located opposite the photocathode, and the rear face opposite the resistive anode.

Figure 3:
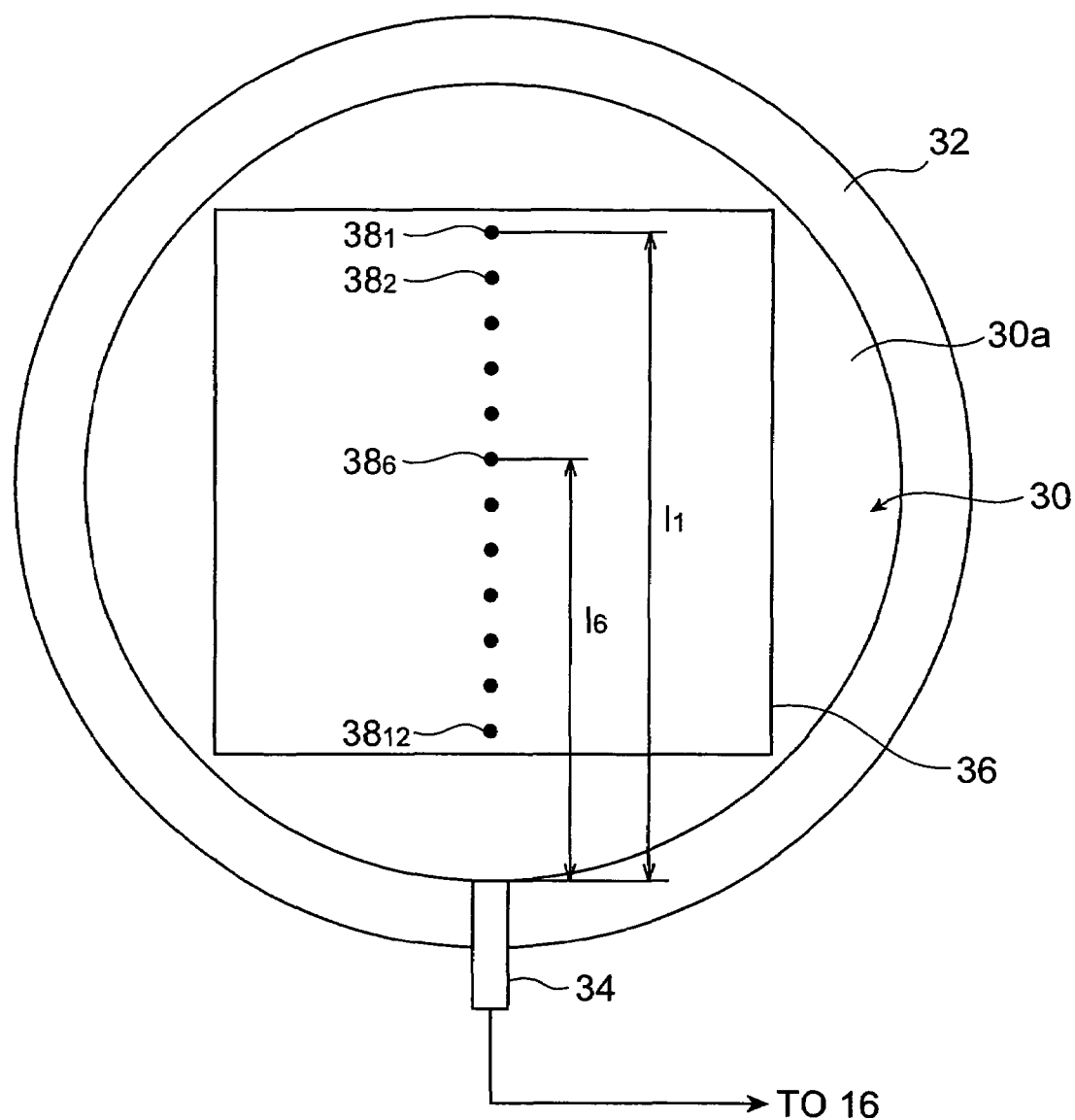
FIG. 3 is a schematic plan view showing a micro channel plate.

FIG. 3 is a schematic plan view showing the micro channel plate. For simplicity of the drawing, FIG. 3 is illustrated without illustration of channels in the micro channel plate. The both end faces of the micro channel plate 30 are provided with an evaporated electroconductive material as electrodes 30a. The periphery of the micro channel plate 30 is covered with a metal flange 32 of ring shape. A lead terminal 34 is attached to one location on the flange 32. The lead terminal 34 is electrically conductive to the electrode 30a on the end face of the micro channel plate 30. The lead terminal 34 is connected to a position-time measuring circuit 16 by a lead wire. As described later, the micro channel plate 30 generates an electric pulse signal in synchronization with a timing at which light is detected. This pulse signal is fed to the circuit 16 through the lead terminal 34.

The position-time measuring circuit 16 is electrically connected to both the tester 12 and the photomultiplier tube 14. The circuit 16 acts as a position calculator for calculating a detection position using a signal fed from the photomultiplier tube 14. In addition, the circuit 16 also acts as a time difference measuring device for measuring the time difference between the reference time pulse fed from the tester 12 and the detection timing pulse fed from the photomultiplier tube 14. This time difference indicates a detection time with respect to the reference time pulse. The detection position and the detection time determined by the circuit 16 are fed to the data processor 18.

The data processor 18 receives the detection position and detection time from the position-time measuring circuit 16 and stores them in association with each other. The processor 18 is, for example, a personal computer. The processor 18 has a CPU, storage device, keyboard, mouse, and display. The storage device stores a data processing program to be executed by the CPU.

The operation of the time-resolved measurement apparatus 100 will now be described. When the tester 12 activates the inverter chain 20 on the sample 10, the plurality of inverters 22 operate in turn at intervals of about 70 ps. At this time, transistors in the inverters 22 emit light 15 with a certain probability. The photomultiplier tube 14 receives the light 15 on the photocathode. The photocathode converts the light 15 into a photoelectron by photoelectric effect. The photoelectron travels to the front face or input face of the micro channel plate by an electric field applied between the photocathode and the micro channel plate. The incidence position of the photoelectron on the micro channel plate corresponds to the incidence position of the light 15 on the photocathode.

The micro channel plate generates at least one secondary electron at the incidence position of the photoelectron and multiplies the secondary electron while maintaining the two-dimensional position thereof. More specifically, the micro channel plate has a structure in which a number of very thin glass pipes are bundled. These glass pipes are channels. The inner wall of each channel is an electric resistor, and is an electron emitter also. The individual channels act as independent electron multipliers. When a quantum (e.g., a photoelectron in the present embodiment) to which the micro channel plate is sensitive is incident on the inner wall of one channel, at least one electron is emitted from the inner wall. The electron thus emitted is accelerated by an electric field applied between the two end faces of the micro channel plate, again collides with the inner wall, and results in emission of secondary electrons. The secondary electrons travel along the channel while repeating collision with the inner wall, to be multiplied thereby. The two-dimensional position of secondary electrons is maintained by the channel. When the secondary electrons reach the rear face of the micro channel plate, they are emitted from the rear face or output face of the micro channel plate by an electric field applied between the micro channel plate and the resistive anode, and collected to the resistive anode.

The resistive anode is an electrical conductor plate provided with a uniform resistive layer on one surface. Electrodes for signal readout are provided at four positions in the periphery of the resistive anode. These electrodes are electrically connected to the position-time measuring circuit 16. When the secondary electrons enter the resistive anode, these reading electrodes emit charge pulses. The two-dimensional position of the secondary electrons incident on the resistive anode can be determined according to the amounts of charge of these charge pulses. In this manner, the resistive anode generates a signal according to the position at which the light 15 is detected and feeds the signal to the position-time measuring circuit 16.

The circuit 16 receives the charge pulses from the electrodes at the four corners of the resistive anode in the photomultiplier tube 14, and calculates the two-dimensional position of the secondary electrons on the resistive anode by detection of the weighted center. This two-dimensional position corresponds to the two-dimensional position of the light emission on the sample 10. The position at which the light 15 is detected is determined in this manner. This detection position is sent to the data processor 18.

Furthermore, the photomultiplier tube 14 generates a pulse in synchronization with a timing at which the light 15 is detected. This detection timing pulse is taken out of the micro channel plate 30. The generation of the detection timing pulse will be described below with reference to FIG. 3.

A square region indicated by reference numeral 36 is a region in which the secondary electrons can be collected by the resistive anode in the rear face (output face) of the micro channel plate 30. This region will be referred to hereinafter as "effective region." When the inverters $22_1$-$22_{12}$ emit light, photoelectrons are collected at positions $38_1$-$38_{12}$ in the effective region 36 corresponding to the respective inverters $22_1$-$22_{12}$. As secondary electrons are emitted from each of these positions 38 to the resistive anode, the potential instantaneously increases on the output face of the micro channel plate 30. Subsequently, electrons flow from an electric circuit, which is connected to the micro channel plate 30, to each position 38, to return the potential of the output face soon to a predetermined steady potential. This flow of electrons is the aforementioned detection timing pulse. This pulse propagates on the output face of the micro channel plate 30 and travels to the position-time measuring circuit 16 through flange 32, lead terminal 34, and the foregoing electric circuit, i.e., the pulse reading circuit.

The circuit 16 receives the reference time pulse from the tester 12 immediately after the tester 12 activates the inverter chain 20 on the sample 10. Thereafter, the circuit 16 receives the detection timing pulse from the micro channel plate 30. The circuit 16 has a time-to-amplitude converter (TAC), and the reference time pulse and the detection timing pulse are fed to this time-to-amplitude converter. The time-to-amplitude converter generates a voltage signal having a level corresponding to the time difference between the reference time pulse and the detection timing pulse. As described above, this time difference is equivalent to the detection time of the light 15 with respect to the time of excitation of the sample 10. This signal corresponding to the time difference will be referred to hereinafter as "detection time signal." The detection time signal is fed from the circuit 16 to the data processor 18.

The data processor 18 receives the detection position and the detection time signal from the circuit 16, corrects the detection time indicated by the detection time signal, and thereafter stores the detection position and the detection time in association with each other in the storage device. The correction for the detection time will be described later in detail.

Since the probability at which a transistor emits light upon its switching is very small, the sample 10 is repeatedly excited to accumulate the detection positions and the detection times in the data processor 18. The accumulated data can be utilized in various ways. For example, the data processor 18 can be arranged to count the number of light emissions at each detection position over a certain period of time and generate a two-dimensional image in which luminances according to the counted numbers are assigned to pixels corresponding to the detection positions. Also, the data processor 18 can be arranged to create a histogram of the detection times at a specific detection position, using the accumulated detection times. In this histogram, the horizontal axis represents the detection times and the vertical axis the number of light emissions. A peak in the histogram indicates a time at which light emissions at a specific detection position are detected at a high frequency. Therefore, the detection time corresponding to the peak can be regarded as a timing of the switching of the transistor corresponding to the detection position in the inverter 22. By calculating detection times corresponding to peaks in the histograms for the detection positions corresponding to the respective inverters 22, it is feasible to find the operation timings of a sequence of inverters 22. This enables an analysis of operation of the inverter chain 20.

The following will describe the reason why the detection time is corrected in the data processor 18, and, thereafter, will concretely describe the correction process. In the beginning, the inventors arranged the data processor 18 so as to store the detection position and the detection time without correction for the time difference. However, the inventors realized that this was unfavorable for the analysis of the sequential operation timings of multiple semiconductor devices such as the inverters $22_1$-$22_{12}$. This will be described with reference to FIGS. 4 and 5.

Figure 4:
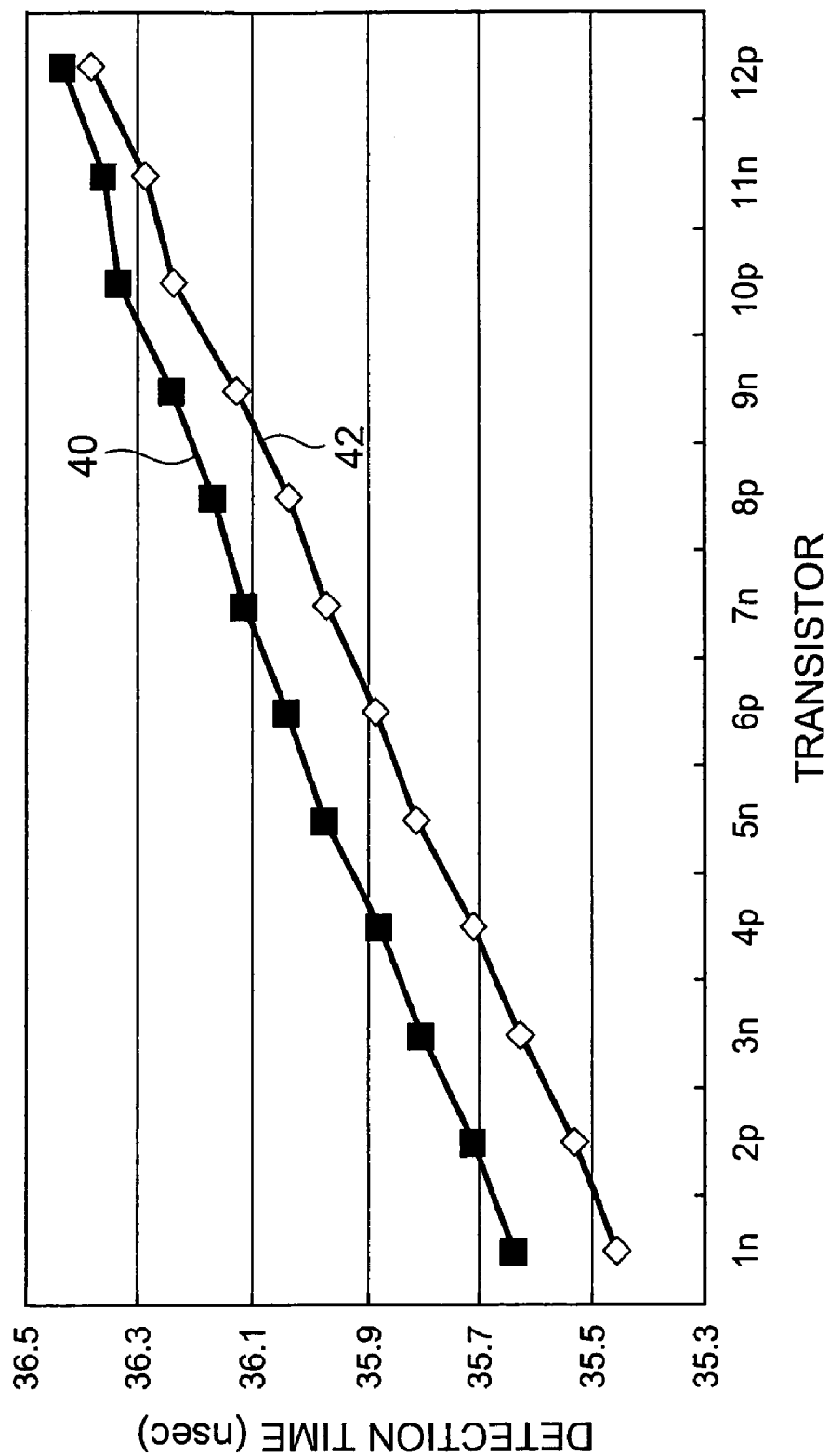
FIG. 4 is a diagram showing emission timings of transistors in inverters.
Figure 5:
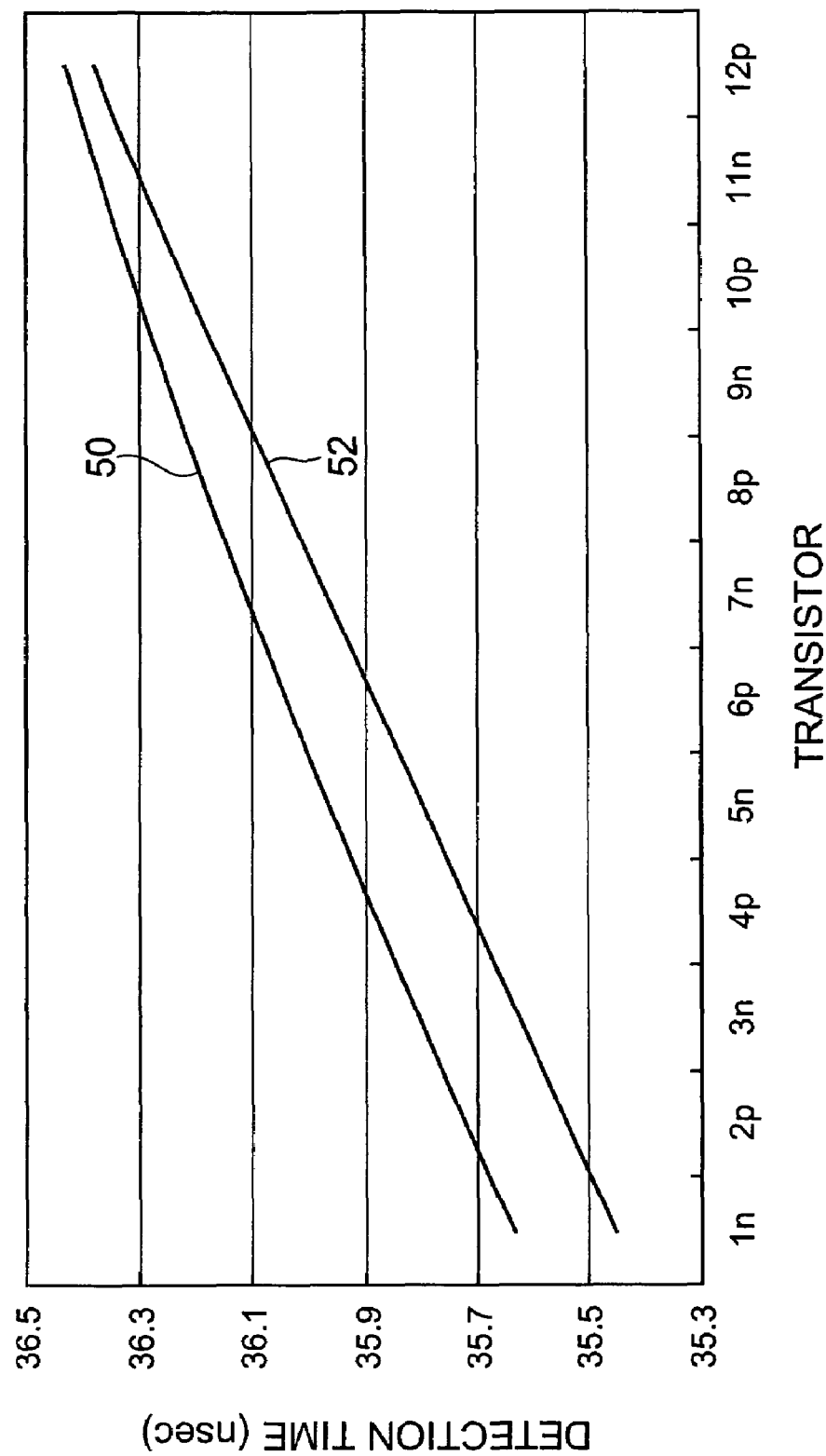
FIG. 5 is a diagram showing approximate curves of sequential line graphs shown in FIG. 4.

FIG. 4 shows light emission timings of the inverters $22_1$-$22_{12}$ on the basis of data acquired in both the case with the correction for detection times and the case without the correction. In FIG. 4, numeral 40 denotes the emission timings in the case without the correction for detection times, and 42 the emission timings in the case with the correction for detection times. FIG. 5 shows approximate curves of these sequential line graphs 40 and 42. In FIG. 5, numeral 50 denotes an approximate curve in the case without the correction for detection times, and 52 an approximate curve in the case with the correction for detection times. In these graphs, the horizontal axis represents the transistors in the inverters $22_1$-$22_{12}$, and the vertical axis the detection times. On the horizontal axis, $1n$, $3n$, $5n$, $7n$, $9n$, and $11n$ represent n-FETs in the respective inverters $22_1$, $22_3$, $22_5$, $22_7$, $22_9$, and $22_{11}$, and $2p$, $4p$, $6p$, $8p$, $10p$, and $12p$ p-FETs in the respective inverters $22_2$, $22_4$, $22_6$, $22_8$, $22_{10}$, and $22_{12}$. The detection times on the vertical axis are determined as described above: a histogram is created for each inverter 22, using the detection positions and detection times accumulated in the data processor 18, and the detection time corresponding to a peak in the histogram is acquired by calculation.

As described above, the inverter chain 20 is designed so that the transistors in the inverters $22_1$-$22_{12}$ are sequentially subjected to switching at constant time intervals. Therefore, the slope of graph 50 must be constant as long as the measurement is accurate. In fact, however, the slope of graph 50 decreases as the transistor is located nearer the lead terminal 34. This means that the time interval of switching becomes gradually shorter in the result of the measurement.

The inventors contemplates that the nonuniformity of switching timings in the result of the measurement is error due to variation in the propagation time of the detection timing pulse on the micro channel plate 30. This will be described below.

As shown in FIG. 3, the distance between the position 38 at which a detection timing pulse is generated and the lead terminal 34 differs depending on the position of the inverter 22. For this reason, detection timing pulses generated by photons emitted from different inverters 22 require different times for propagation from their generation position 38 to the lead terminal 34. For example, as shown in FIG. 3, the distance between detection position $38_1$ corresponding to light emission of inverter $22_1$, and lead terminal 34 is $1_1$, and the distance between detection position $38_6$ corresponding to light emission of inverter $22_6$, and lead terminal 34 is $1_6$. With simple consideration, therefore, it is presumed that there is a difference of $(1_1 - 1_6)/c$ between the times necessary for propagation of the detection timing pulses from the respective detection positions $38_1$ and $38_6$ to the lead terminal 34. The symbol "c" herein represents the speed of electromagnetic waves. The detection time delays from a time at which the light 15 is actually detected, i.e., a time at which the detection timing pulse is generated, by a time necessary for the detection timing pulse to propagate to the position-time measuring circuit 16. It is considered that since the delay differs depending on the detection positions $38_1$-$38_{12}$, the time intervals of the measured switching timings become nonuniform. The propagation time of each detection timing pulse is intricately affected by various factors, such as the shape of the flange 32, the stricture and material of the micro channel plate 30, and so on.

The number of the lead terminals does not have to be limited to 1, but a plurality of lead terminals may be installed for reduction in the absolute value of the delay (decrease in the distance from detection position 38 to lead terminal 34). In that case, the lead terminals preferably have the same length. An example in which the number of the lead terminals 34 is infinite is to use a cone electrode instead of the lead terminals, whereby the absolute value of the delay can be minimized.

Figure 6:
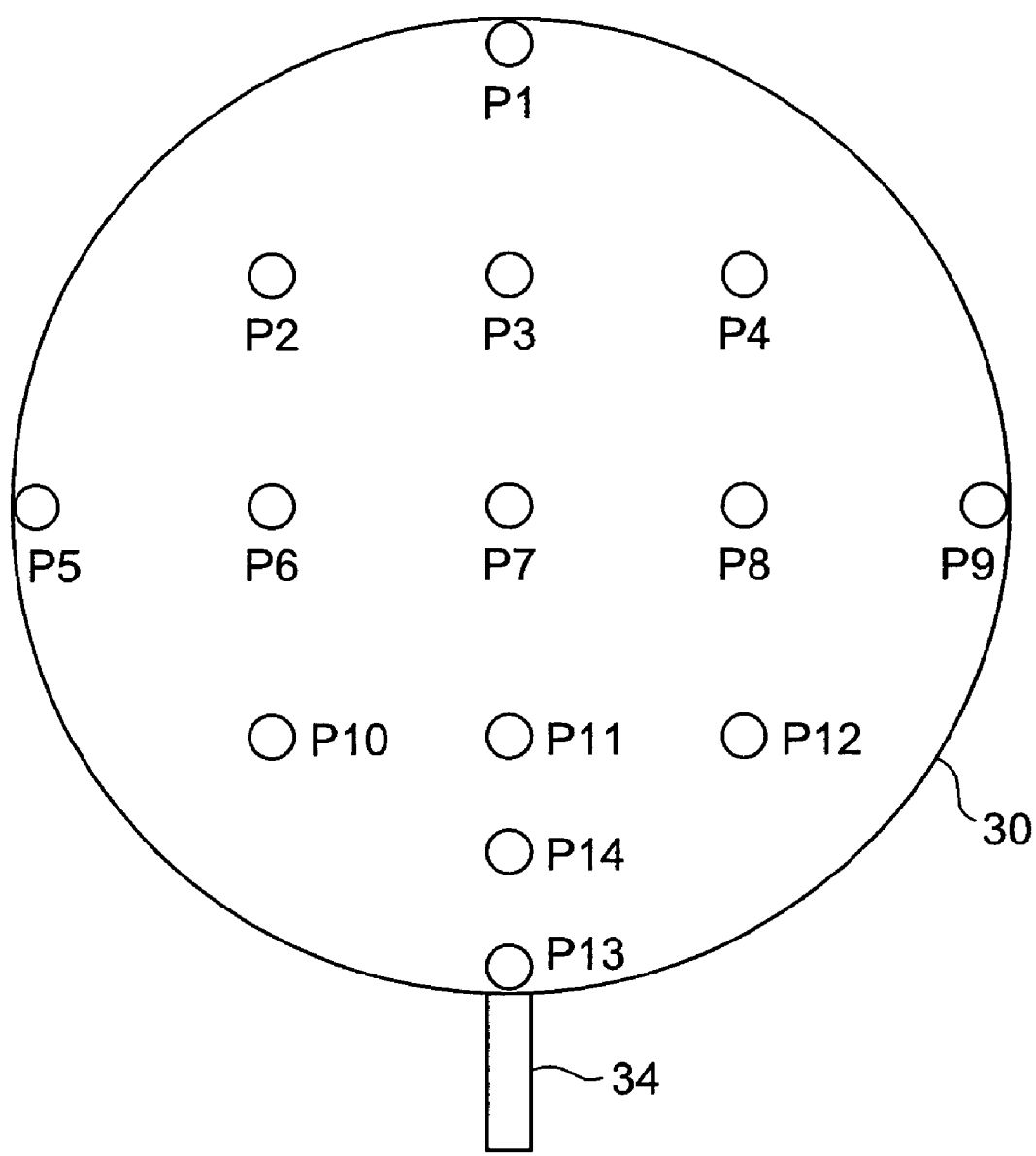
FIG. 6 is a schematic plan view showing a plurality of detection positions on a surface of a micro channel plate.
Figure 7:
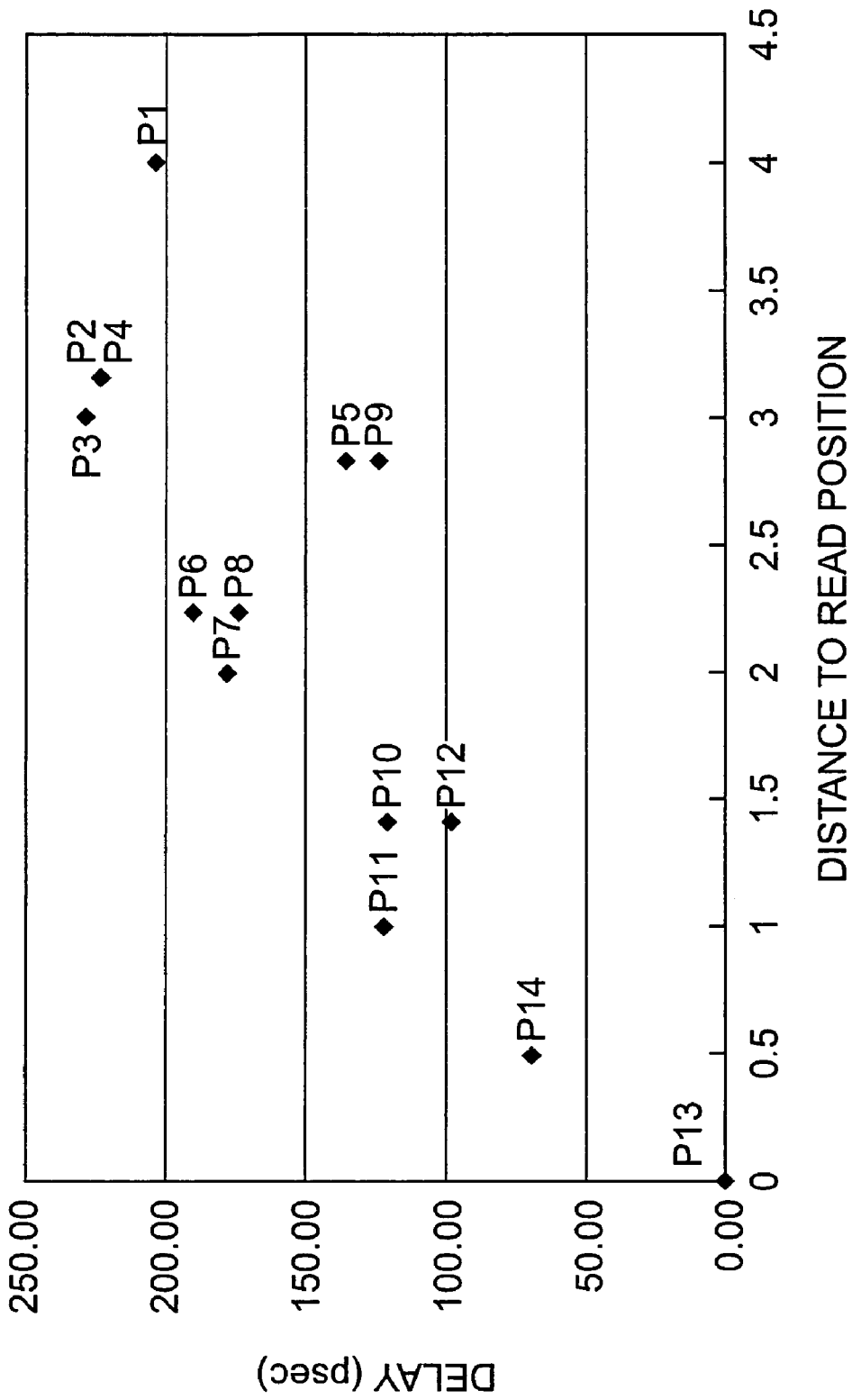
FIG. 7 is a diagram showing the distribution of delays of detection times corresponding to a plurality of detection positions.

FIG. 6 is a schematic plan view showing a plurality of detection positions P1-P14 on the micro channel plate 30, and FIG. 7 depicts the delays of the detection times corresponding to those positions. For simplicity of the drawing, FIG. 6 is illustrated without illustration of the channels of the micro channel plate 30. The distribution of the delays shown in FIG. 7 reflects that the time to arrival at the lead terminal 34 becomes longer as the detection timing signal is generated at a position more distant from the lead terminal 34. The delays corresponding to the respective detection positions can be calculated using an electromagnetic field simulator or a high-frequency circuit simulator, or can be measured by a method as described later.

The variation in the delays of the detection times according to the detection positions causes no problem in use in which light emitted from one location on the sample 10 is repeatedly measured. However, a problem will arise in the case of analyzing the sequential operation timings of multiple semiconductor devices located at different positions, as in the case of the inverter chain 20. As shown in FIG. 3, as the inverter 22 becomes nearer the last one, it generates the detection timing pulse at the detection position 38 nearer the output terminal 34. Therefore, the inverter 22 nearer the last one has a shorter delay of the detection time. This nonuniformity of the delays produces the result of the measurement that the switching intervals, which should be constant, become gradually shorter.

In view of this, the inventors decided to arrange the data processor 18 so as to correct the variation in the delays according to the detection positions. This correction process is carried out using correction data that reflects the distribution of the delays on the micro channel plate 30. This correction data can be acquired by experiment, or can also be acquired by calculation using an electromagnetic field simulator or high-frequency circuit simulator.

Figure 8:
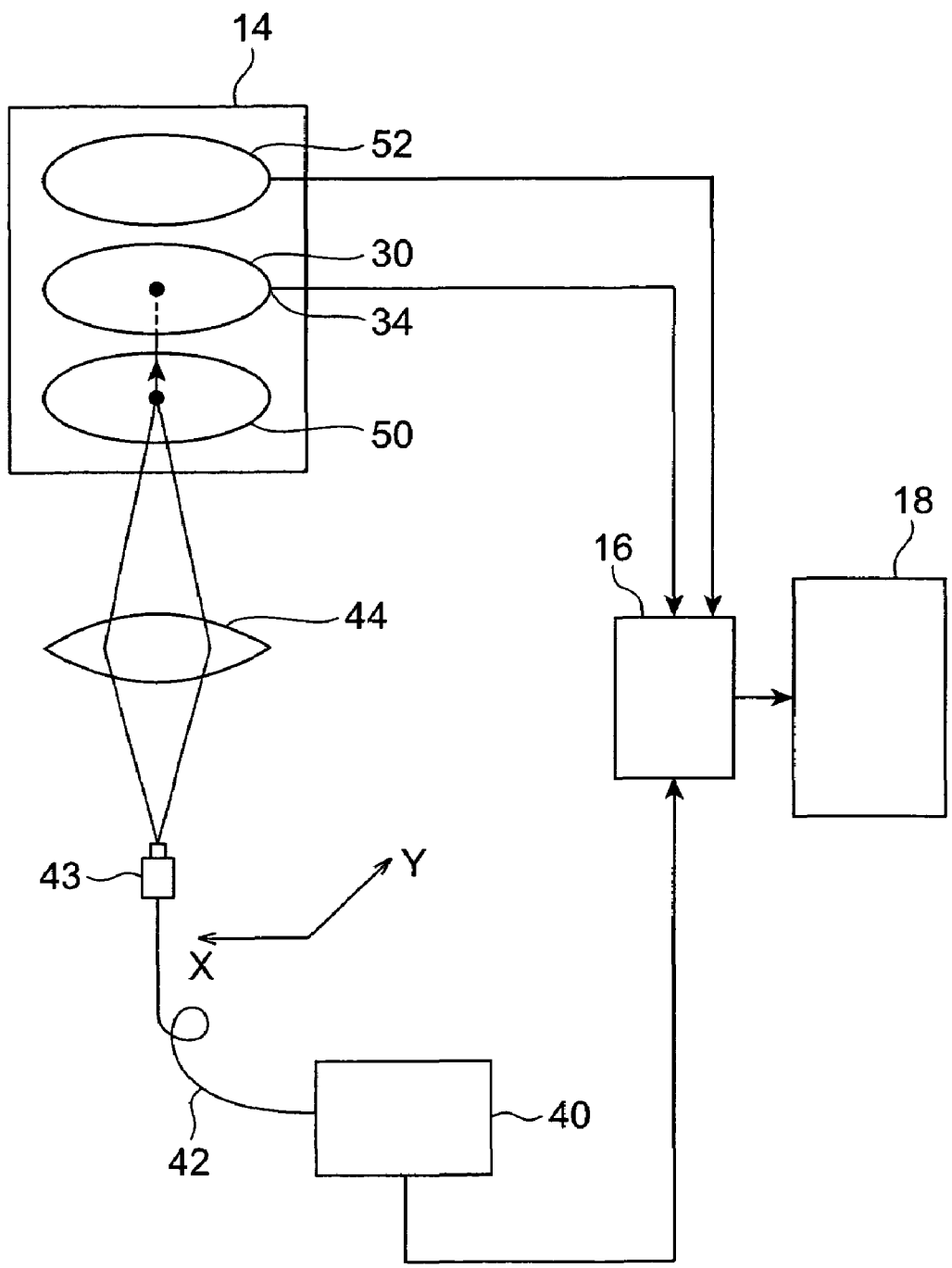
FIG. 8 is a schematic view for explaining a method of measuring correction data.

An example of a method of measuring the correction data will be described below. FIG. 8 is a schematic view showing the measurement method. In this method, a picosecond or subnanosecond pulse laser light source 40 is used instead of the tester 12 in the time-resolved measurement apparatus 100, and the distribution of the delays according to the detection positions of the laser light is determined. The laser light source 40 emits pulsed laser light and outputs a time reference signal in synchronization with the emission. This time reference signal is fed to the position-time measuring circuit 16. An optical fiber 42 is connected to the light source 40. The pulsed laser light emitted from the light source 40 propagates in the optical fiber 42 and emerges toward a lens 44. The laser light is focused by the lens 44 to enter a photocathode 50 of the photomultiplier tube 14. Photoelectrons generated by photoelectric effect in the photocathode 50 are multiplied by the micro channel plate to be emitted toward a resistive anode 52. The detection timing pulse generated at this time propagates on the rear face of the micro channel plate 30 to reach the lead terminal 34, and is then fed therefrom to the position-time measuring circuit 16. The resistive anode 52 feeds a signal corresponding to the detection position of the laser pulsed light, to the circuit 16. The circuit 16 calculates the detection position on the basis of the signal from the resistive anode and sends the calculated detection position to the data processor 18. In addition, the circuit 16 generates a signal corresponding to the time difference between the time reference pulse from light source 40 and the detection timing pulse, and sends the signal to the data processor 18. In this method, this time difference will be treated as the delay of the detection time according to the detection position. The data processor 18 stores the detection position and the delay sent from the circuit 16, in association with each other. The light is made incident to various positions on the photocathode 50 with two-dimensional movement of the output end 43 of the optical fiber using an X-Y stage (not shown), so as to accumulate the detection positions and the delays in the data processor 18.

The data processor 18 assigns 512×512 pixels, i.e., approximately 260,000 pixels to the effective region 36 on the micro channel plate 30. A way of measuring the delay for each pixel by irradiating each pixel with the light is not practical because an extremely huge amount of time is necessary even if the measurement time per pixel is set to about 10 seconds. In view of this, it is effective to measure the delays for only several ten pixels and to calculate delays for the other pixels by interpolation.

Figure 9:
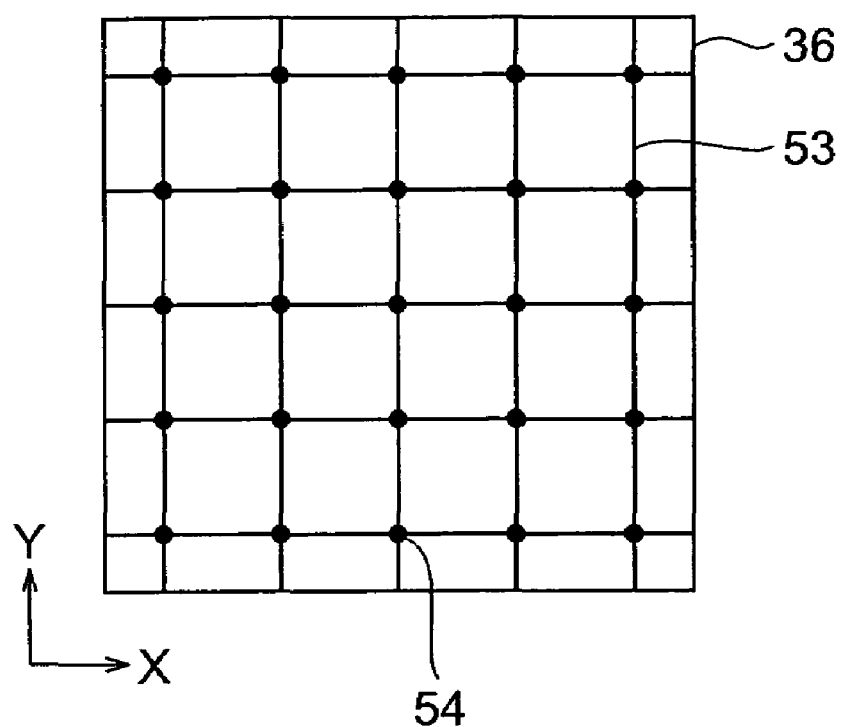
FIG. 9 is a diagram showing sampling points on an effective region.
Figure 10:
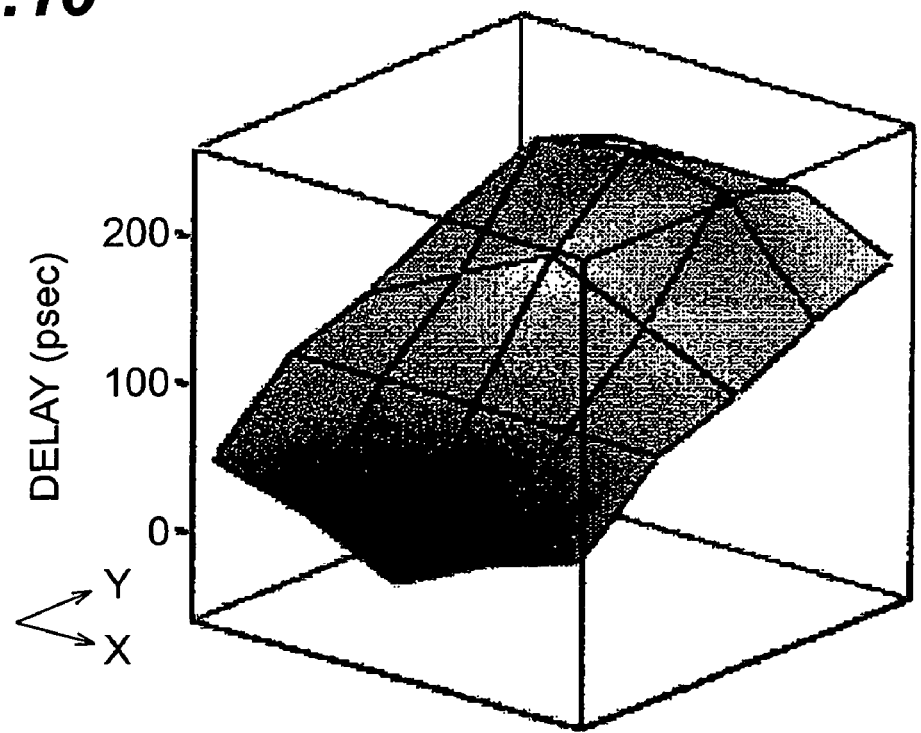
FIG. 10 is a diagram showing a 3D display of delays of detection times measured at the sampling points.
Figure 11:
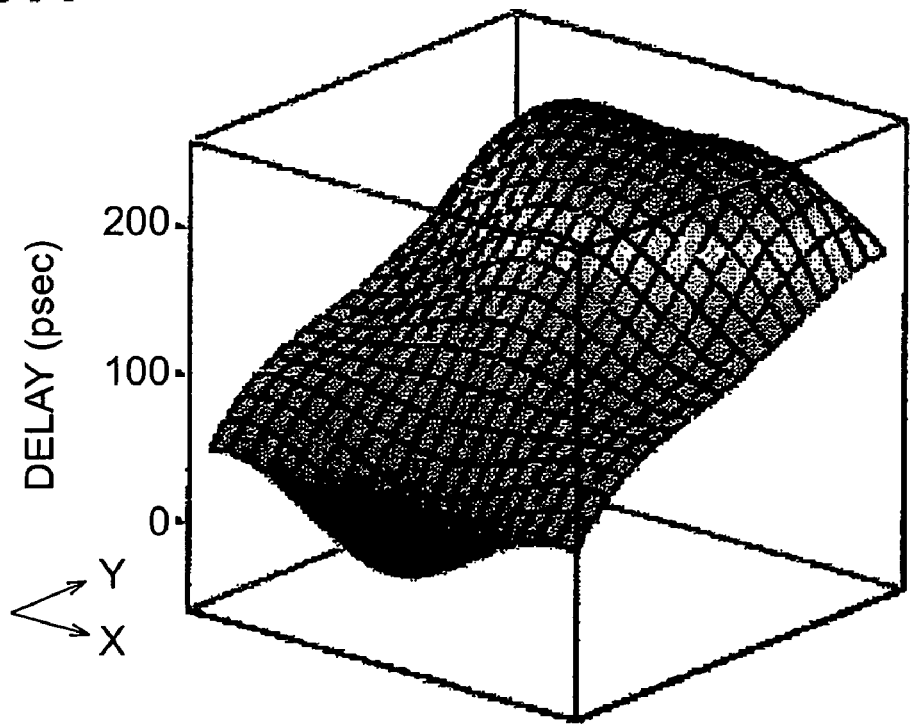
FIG. 11 is a diagram showing a 3D display of delays after interpolation.

More specifically, as shown in FIG. 9, the effective region 36 is divided by a hypothetical mesh 53 and the delays are measured for only twenty five intersections 54 in the mesh 53. Namely, these intersections 54 are sampling points. FIG. 10 depicts a 3D display of the distribution of the delays measured at the sampling points 54. The delays corresponding to the positions between the sampling points 54 are calculated by two-dimensional spline interpolation. FIG. 11 depicts a 3D display of the distribution of the delays obtained by the interpolation. This interpolated delay distribution is used as correction data.

Figure 12:
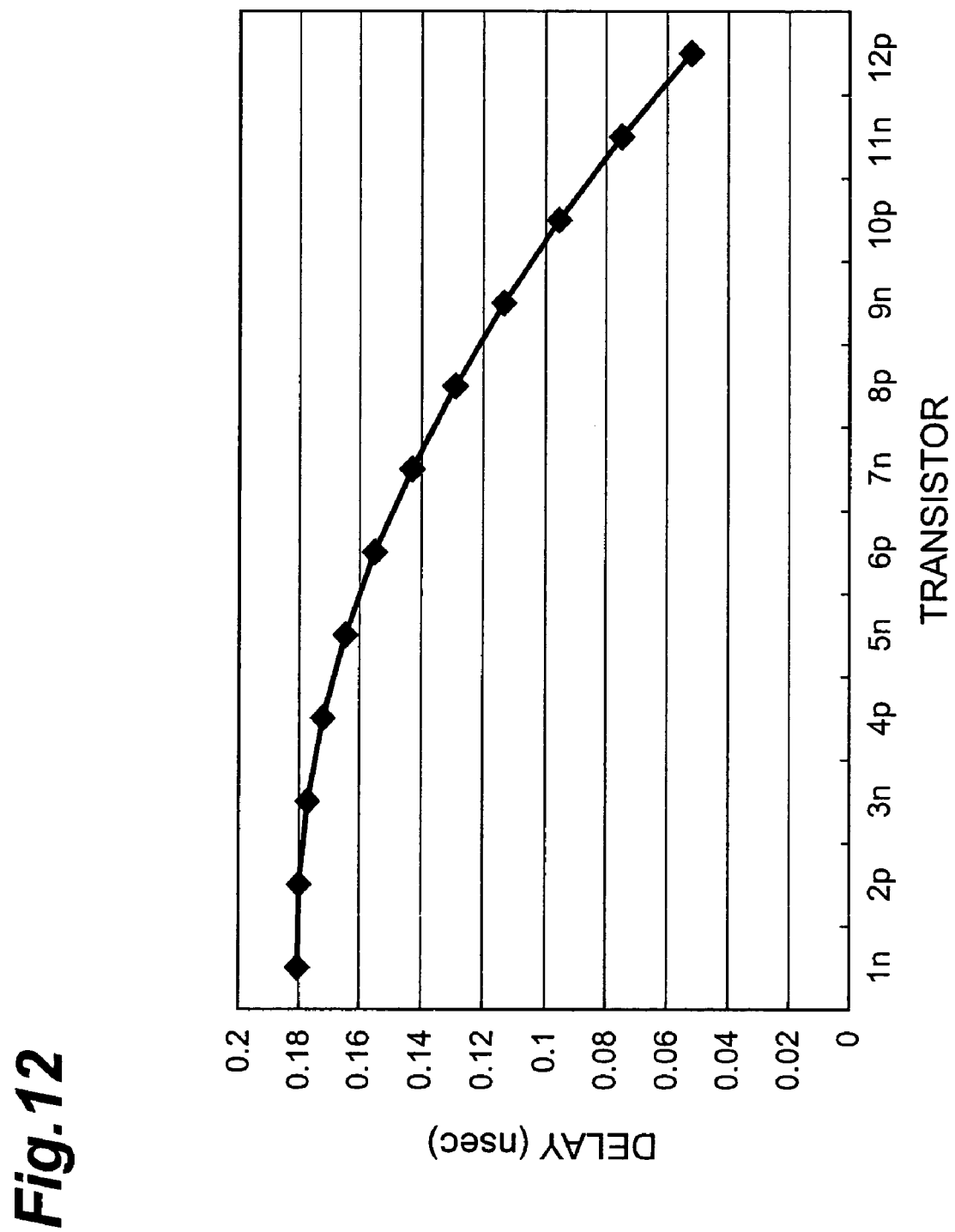
FIG. 12 depicts the distribution of delays of detection times corresponding to the transistors in an inverter chain.

FIG. 12 shows the delays corresponding to the transistors in the inverter chain 20 determined on the basis of the correction data shown in FIG. 11. As shown in FIG. 12, a transistor in an earlier position has a greater delay.

The data processor 18 acquires a detection time from the circuit 16 by the time-resolved measurement of the sample 10 and thereafter subtracts the correction data from the detection time. Namely, the delay for each detection position is subtracted from the detection time for the same detection position. This subtraction removes the propagation time of the detection timing pulse from the detection time. Thus, it is possible to correct the error of the detection time due to the variation in the propagation time of the detection timing pulse. The data processor 18 stores the detection time thus corrected, in association with the detection position. Therefore, it is feasible to enhance the precision of the time-resolved measurement. Indeed, as indicated by graph 42 in FIG. 4 and graph 52 in FIG. 5, this correction arranges the detection times of light emissions from the transistors in the inverters $22_1$-$22_{12}$ at approximately equal intervals, so as to achieve agreement with the design theory.

Figure 13:
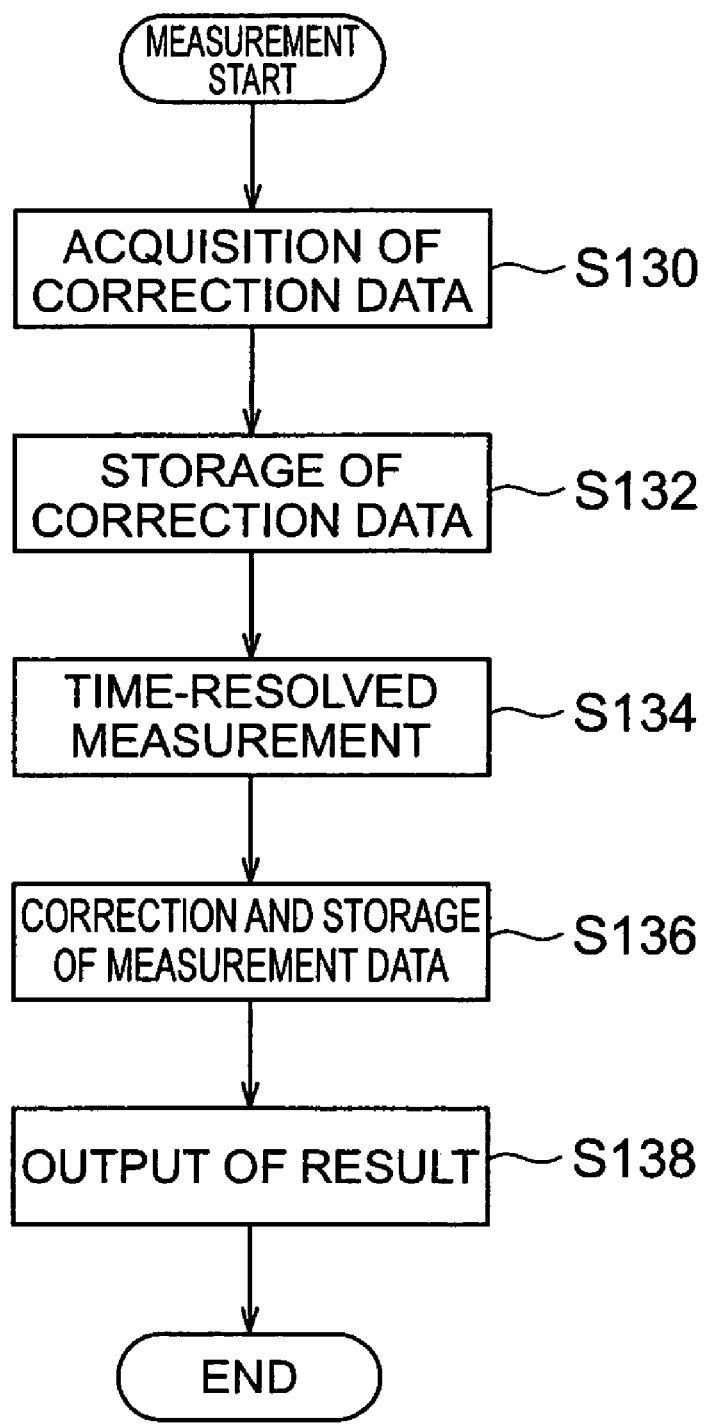
FIG. 13 is a flowchart showing an example of the procedure of time-resolved measurement.
Figure 14:
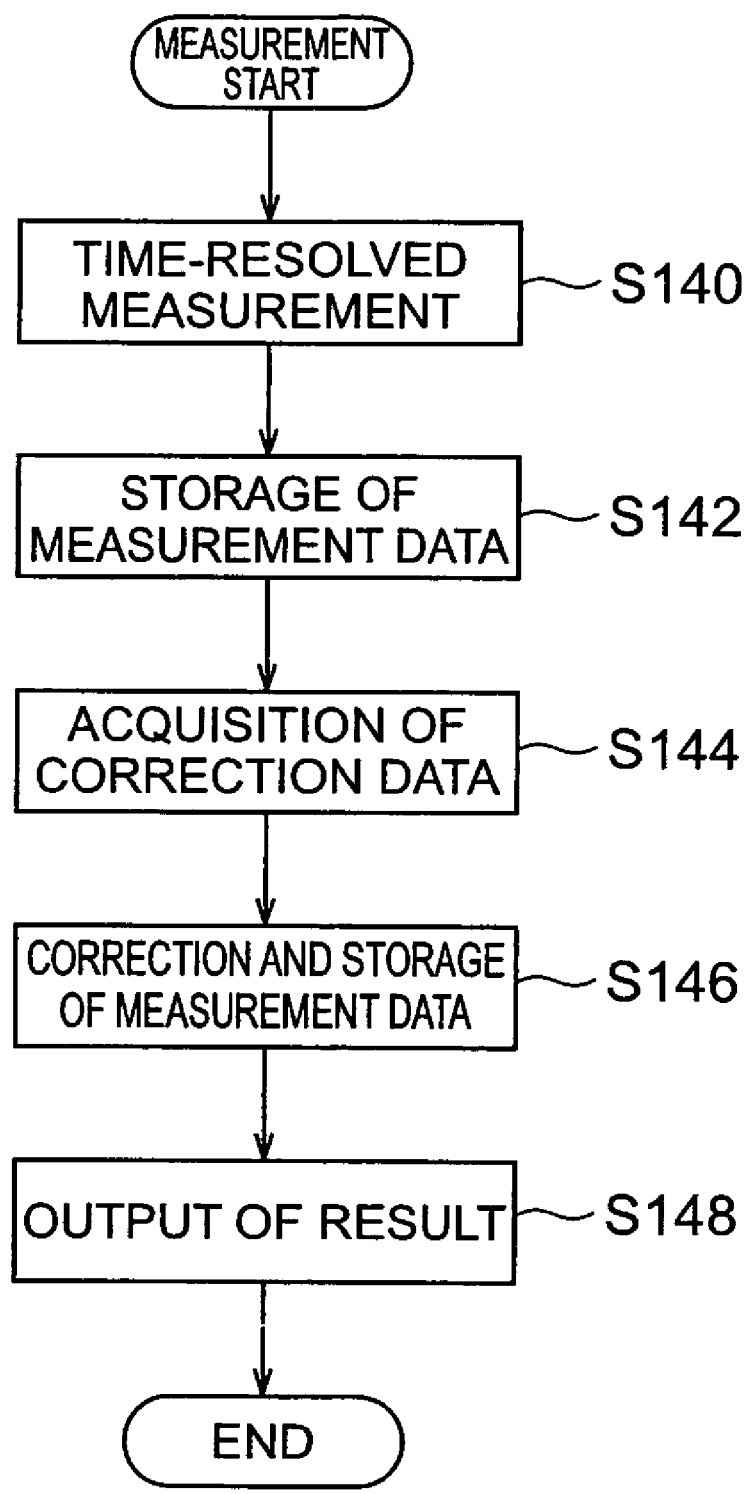
FIG. 14 is a flowchart showing another example of the procedure of time-resolved measurement.

The acquisition of the correction data may be done before the time-resolved measurement of sample 10 as shown in FIG. 13, or may be done after the time-resolved measurement as shown in FIG. 14.

In the procedure shown in FIG. 13, the first step is to acquire the correction data by the method described above with reference to FIG. 8 (step S130). This correction data is stored in the storage device in the data processor 18 (step S132). Thereafter, the apparatus 100 performs the time-resolved measurement of light emission from the inverter chain 20 by the method described above with reference to FIG. 1 (step S134). The data processor 18 subtracts the correction data from the acquired measurement data to correct the time error in the measurement data (step S136). The measurement data after the correction is stored in the storage device and is also displayed in the form of a sequential line graph as shown in FIG. 4, on the display of the data processor 18 (step S138).

On the other hand, in the procedure shown in FIG. 14, the first step is to perform the time-resolved measurement of the inverter chain 20 by the apparatus 100 (step S140), and the next step is to store the obtained measurement data in the storage device in the data processor 18 (step S142). Thereafter, the correction data for time error is acquired by the method shown in FIG. 8 (step S144). The data processor 18 reads the measurement data from the storage device and subtracts the correction data therefrom to correct the time error (step S146). The corrected measurement data is stored in the storage device and is also displayed on the display (step S148).

The above detailed the present invention on the basis of the embodiments thereof. It is, however, noted that the present invention is by no means intended to be limited to the above embodiments. The present invention can be modified in various ways without departing from the scope thereof.

In the above embodiments, the correction data is acquired by the measurement shown in FIG. 8. However, the correction data may be acquired by calculation. For example, the foregoing delay distribution can be calculated using an electromagnetic field simulator or high-frequency circuit simulator.

In this specification, a "photomultiplier tube (PMT)" is one of the embodiments of an "electron multiplier tube (EMT)." The embodiments mentioned above use the position-sensitive photomultiplier tube (PS-PMT). However, for the present invention, it is possible to use any other position-sensitive electron multiplier tube (PS-EMTs) depending on the type of the quantum beam emitted from the sample. It is well known that the micro channel plates are not sensitive only to electron beams but are also sensitive directly to other quantum beams, such as ultraviolet rays (UV and VUV), X-rays, α-rays, charged particles, and neutrons. Which of a PS-PMT and a PS-EMT is to be used is properly determined depending on the type of a quantum beam emitted from an object to be detected.

The above embodiment uses the resistive anode 28 as a position-sensitive anode. Alternatively, it is also possible to use any other position-sensitive anodes, e.g., multi-anodes, a CR chain type anode, a cross-wire anode, and a semiconductor position-sensitive detector (PSD). The position of secondary electrons may also be measured by using a fluorescent screen, as an anode, for converting the secondary electrons into an optical image and taking the optical image by use of an image sensor. The fluorescent screen may be fiber-coupled with the image sensor through a fiber plate. These position detections may be one-dimensional or two-dimensional.

The embodiments mentioned above take up the analysis of the operation of the semiconductor integrated circuit. However, the time-resolved detection according to the present invention can be applied to a wide variety of applications, and the present invention can be applied to various measurement techniques including Time of Flight (TOF) application, e.g., secondary ion mass spectroscopy (SIMS), ion scattering spectroscopy (ISS), an atom probe, and so on.

INDUSTRIAL APPLICABILITY

The time-resolved measurement apparatus of the present invention corrects the nonuniformity of the detection time delay according to the detection position, whereby it is able to cancel the error of the detection time and to enhance the precision of the time-resolved measurement.

The invention claimed is:

1. A time-resolved measurement apparatus for acquiring position information and timing information of a quantum beam generated due to excitation of a sample, comprising:
   a signal generator for generating a reference time pulse in synchronization with the excitation of the sample;
   a detector for detecting the quantum beam and for generating a position signal corresponding to a detection position, and a detection timing pulse synchronized with a detection timing;
   a position calculator for calculating the detection position using the position signal;
   a time difference measuring device for measuring a time difference between the reference time pulse and the detection timing pulse; and
   a data processor for storing the detection position calculated by the position calculator and the time difference measured by the time difference measuring device, in association with each other,
   the detector having a position-sensitive electron multiplier tube,
   the electron multiplier tube having a micro channel plate for generating an electron at a position corresponding to an incidence position of the quantum beam on the electron multiplier tube and for multiplying the electron while maintaining the position, and an output terminal electrically connected to the micro channel plate,
   the detection timing pulse being generated in response to a potential change that occurs when the electrons multiplied by the micro channel plate are emitted from the micro channel plate, and being fed from the micro channel plate to the time difference measuring device through the output terminal, and
   the data processor correcting the time difference according to a distance between a position at which the detection timing pulse is generated on the micro channel plate and the output terminal, and storing the corrected time difference in association with the detection position.

2. A time-resolved measurement apparatus according to claim 1, wherein the data processor removes a time necessary for the detection timing pulse to travel from the position at which the detection timing pulse is generated to the output terminal, from the time difference measured by the time difference measuring device, thereby correcting the time difference.

3. A time-resolved measurement apparatus according to claim 1, wherein the data processor sets a plurality of sampling points on the micro channel plate, acquires and interpolates correction data for the detection timing pulse generated at each sampling point, and corrects the time difference using the interpolated correction data.

4. A time-resolved measurement apparatus according to claim 1, wherein the data processor accumulates the detection position and the time difference over plural times of the excitation of the sample.

5. A time-resolved measurement apparatus according to claim 4, wherein the data processor uses the accumulated time differences to create a histogram of the time differences associated with a specific detection position.

6. A time-resolved measurement apparatus according to claim 5, wherein the sample has a circuit including a plurality of semiconductor devices that can emit the quantum beams upon their operation,
   wherein the excitation of the sample is to activate the circuit to operate the semiconductor devices in turn, and
   wherein the data processor specifies the detection positions corresponding to the positions of the semiconductor devices, and calculates the time differences corresponding to peaks in the histograms for the specified detection positions.

7. A time-resolved measurement apparatus according to claim 1, wherein the position-sensitive electron multiplier tube is a position-sensitive photomultiplier tube having a photocathode for converting the quantum beam into a photoelectron by photoelectric effect, and
   wherein the micro channel plate is located opposite the photocathode and configured to receive the photoelectron from the photocathode to generate and multiply secondary electrons.

* * * * *